United States Patent
Witte

(10) Patent No.: US 8,023,706 B2
(45) Date of Patent: Sep. 20, 2011

(54) AUTOMATICALLY DETERMINING LANDMARKS ON ANATOMICAL STRUCTURES

(75) Inventor: Jens Witte, München (DE)

(73) Assignee: Brainlab AG, Feldkirchen (DE)

( * ) Notice: Subject to any disclaimer, the term of this patent is extended or adjusted under 35 U.S.C. 154(b) by 955 days.

(21) Appl. No.: 11/952,316

(22) Filed: Dec. 7, 2007

(65) Prior Publication Data

US 2008/0260219 A1      Oct. 23, 2008

Related U.S. Application Data

(60) Provisional application No. 60/882,742, filed on Dec. 29, 2006.

(30) Foreign Application Priority Data

Dec. 7, 2006   (EP) .................................... 06025315

(51) Int. Cl.
  *G06K 9/00* (2006.01)
(52) U.S. Cl. ............. 382/128; 128/922; 378/4; 600/414
(58) Field of Classification Search .................. 382/100, 382/128, 129, 130, 131, 132; 128/922; 378/4–27; 600/414, 425, 426
See application file for complete search history.

(56) References Cited

U.S. PATENT DOCUMENTS 5,623,586 A * 4/1997 Hohne ........................ 345/424

OTHER PUBLICATIONS

Cuisenaire et al, "Automatic registration of 3D MR images with a computerized brain atlas", SPIE Medical Imaging, Bd. 2710, 1996, pp. 438-448.

* cited by examiner

*Primary Examiner* — Anand Bhatnagar
(74) *Attorney, Agent, or Firm* — Renner, Otto, Boisselle & Sklar, LLP

(57) ABSTRACT

An automatic landmark determining device, includes a storage device for storing at least one anatomical sample image and at least one anatomical landmark, the at least one anatomical landmark corresponding to a characteristic location within the at least one anatomical sample image, The automatic landmark determining device also includes an input device for inputting an anatomical patient image, and a transformation device. The transformation device is configured to apply an image-adapting transformation to the at least one anatomical landmark, said image-adapting transformation corresponding to a transformation that converts the at least one anatomical sample image to the anatomical patient image.

13 Claims, 7 Drawing Sheets

AUTOMATICALLY DETERMINING LANDMARKS ON ANATOMICAL STRUCTURES

RELATED APPLICATION DATA

This application claims priority of U.S. Provisional Application No. 60/882,742 filed on Dec. 29, 2006, which is incorporated herein by reference in its entirety.

FIELD OF THE INVENTION

The present invention relates generally to anatomical landmarks and, more particularly, to automatically determining landmarks on anatomical structures.

BACKGROUND OF THE INVENTION

Surgical planning software is available that can assist in the planning of a surgical procedure, such as an incision, for altering an anatomical structure. Examples of such software include:

Onyx Ceph 2.5 software
FYI Technologies, Dr. Ceph.
ElleSoft.com, Lightning Ceph
αHAL Software Viewbox 3.1
SimPlant CMF The above examples relate to the cranial bone, in particular the jawbone and facial bones. In such surgical planning software, anatomical landmarks representing typical positions and/or areas for the respective anatomical structure, e.g., a depression, opening and/or a protrusion, are input by the operator (surgeon). Anatomical landmarks are in particular concise formations on a bony or soft-tissue (skin) surface, such as cusps, edges, openings and depressions. Typically, anatomical landmarks are provided in the anatomical structure for muscular attachments, vascular canals, neural canals, etc. Such anatomical landmarks can be displayed using computer tomography (CT) recordings, magnetic resonance tomography (MRT) recordings, x-ray recordings or other diagnostic imaging methods. In the software examples mentioned above, the anatomical landmarks are manually input and can be shown in the diagnostic data of the anatomical structure. The software can display the anatomical structures in two-dimensional or three-dimensional images (models). In these two-dimensional or three-dimensional images, the position of the landmarks can be defined with the aid of operator input. The spatial relationship between these landmarks (e.g., distances, angles, common planes) then can be assessed by the operator by means of a measuring software, for example by means of digital templates, wherein reference is made here, for example, to general standards of harmony (e.g., cosmetic surgery) or to other spatial relationships regarded as being ideal (e.g., relationships between the hip cavity and the femoral head or between the upper and lower jaw).

SUMMARY OF THE INVENTION

The present invention enables a surgical incision, such as an incision on the cranium or jawbone, to be performed in a time-efficient manner. Further, embodiments of the present invention can be used to assist the analysis of the human skeleton of a patient or of the soft-tissue anatomy, as may be done when planning a surgical incision.

An automatic landmark determining device in accordance with the invention preferably includes a sample storing means that stores at least one anatomical sample image along with the corresponding anatomical landmarks. The positions of the landmarks in a two-dimensional or three-dimensional image are thus stored by the sample storing means, in addition to the image data representing an anatomical structure. Image dots or points of the anatomical sample image that match the anatomical landmarks, and in particular which anatomical landmarks are at the respective position, is preferably known. Thus, there preferably is an assignment protocol between the image data representing the anatomical structure and anatomical landmarks, wherein the anatomical landmarks, for example, can be stored as image data together with the anatomical sample image, such that when the anatomical sample image is retrieved and displayed, the anatomical landmarks are displayed along with the sample image. The anatomical landmarks, however, also can be stored separately, for example in a table that specifies the position of the landmark in the sample image and in particular the type of anatomical landmark.

The landmark determining device also preferably includes an input means for inputting an anatomical patient image and/or data set, for example a two-dimensional or three-dimensional image. The anatomical patient image and/or data set preferably show an area of an anatomical structure of the patient, for example the cranial bone or jawbone or hip bone or femoral bone. The anatomical patient image, for example, can be one or a series of x-ray images, CT images or magnetic resonance (MRT) images.

A transformation means is provided that compares (e.g., matches) the input anatomical patient image (patient data set) and the sample image (sample data set). The transformation means can be configured to perform an image-adapting transformation that converts the sample image into the patient image, in particular a continuous or virtually continuous transformation such as is used by morphing algorithms or image fusion algorithms. The image-adapting transformation can be defined by the fact that, as well as possible, it superimposes the sample image and the patient image and/or that it continuously converts (in particular changes or deforms) the sample image into the patient image or converts the sample image into the patient image in steps (using a plurality of steps).

The image-adapting transformation, which converts the sample image into the patient image, can be applied to the landmarks of the sample image. For example, the coordinates of the landmarks defined in the sample image can be subjected to the same morphing algorithm as the other image data of the sample image. The sample image represents an anatomical structure that is to be converted as an anatomical sample structure into the anatomical structure of the patient by the image-adapting transformation, wherein the anatomical landmarks are in particular subjected to the same transformation as the image data situated at the position of the anatomical landmarks. The positions of the landmarks are thus preferably altered by the transformation in exactly the same way as the positions of the sample image data that were situated at the same position as the landmarks before the transformation. Using the transformation, the positions of the landmarks in the patient image are thus obtained. If the positions of the landmarks are stored separately from the sample images, then the positions can be subjected to the image-adapting transformation, so as to determine the position of the landmarks in the patient image.

The transformed landmarks (or the transformed positions of the landmarks) are thus preferably determined or identified as landmarks of the patient image (or as positions of the landmarks in the patient image). Thus, the landmarks for the patient image can be automatically determined. Where "determining the landmarks" is mentioned here, this is intended to mean "determining the positions of the landmarks in the patient image" and/or "identifying or determining image dots in the patient image as landmarks which assume determined positions in the patient image".

The patient images can represent many different anatomical structures of a human or animal body. In order to be able to ascertain the landmarks for a plurality of anatomical structures and/or for a plurality of views of the anatomical structures, the sample storing means preferably comprises a plurality of anatomical sample images representing anatomical structures. The anatomical sample images can already contain the assigned landmarks, for example as image dots and/or image data, or landmarks can be stored separately, which may be assigned to determined positions in the anatomical sample images. The two options cited above are intended to be encompassed here by the term "anatomical sample images together with assigned landmarks".

Once the landmarks of the patient image have been determined, the patient image together with the assigned, determined landmarks are preferably stored. Landmarks and the patient image can likewise be stored such that the determined landmarks are displayed as image data in the patient image and are stored together with other image data of the patient image. Each determined landmark, for example, can be represented in the patient image by a black point or dot. An inscription next to the (e.g., black) dot can likewise be stored, as image data, along with the stored landmarks. The landmarks, together with the position assigned to the landmarks in the patient image, are preferably stored separately. In this way, the landmarks in the patient image can be faded in or out as desired by the operator.

In order to make it easier to assess an anatomical structure and/or make it easier to plan a surgical incision, the landmark determining device can include a means for determining geometric values that depend on the location of the determined landmarks relative to each other and/or describe said relative location. Examples of such geometric values are the distance between two landmarks, the angles between straight lines which connect different landmarks to each other, the location of a plane in which two or more landmarks are situated, the ratio of the distances between different landmarks, etc.

A comparing means is preferably provided that compares the determined geometric values with nominal values. To this end, a nominal value database is preferably provided that stores typical geometric values and/or geometric values that, for example, are regarded as being standard in medical literature. The comparing means preferably compares these nominal values with the determined geometric values relating to the patient image (which can be determined on the basis of the determined landmarks). The comparison result is preferably displayed, for example, as a statement of the percentage deviation between the determined geometric value and the corresponding nominal value. To this end, a display means such as for example a screen is preferably provided.

The landmark determining device can include a computer and a program that, when executed by the computer, realizes the aforesaid landmark determining device in cooperation with the computer.

Also provided herein is a corresponding landmark determining method, wherein the aforesaid program implements said method, and a surgical planning method and corresponding program that employs the landmark determining method.

BRIEF DESCRIPTION OF THE DRAWINGS

The forgoing and other features of the invention are hereinafter discussed with reference to the drawings.

DETAILED DESCRIPTION

Figure 1:
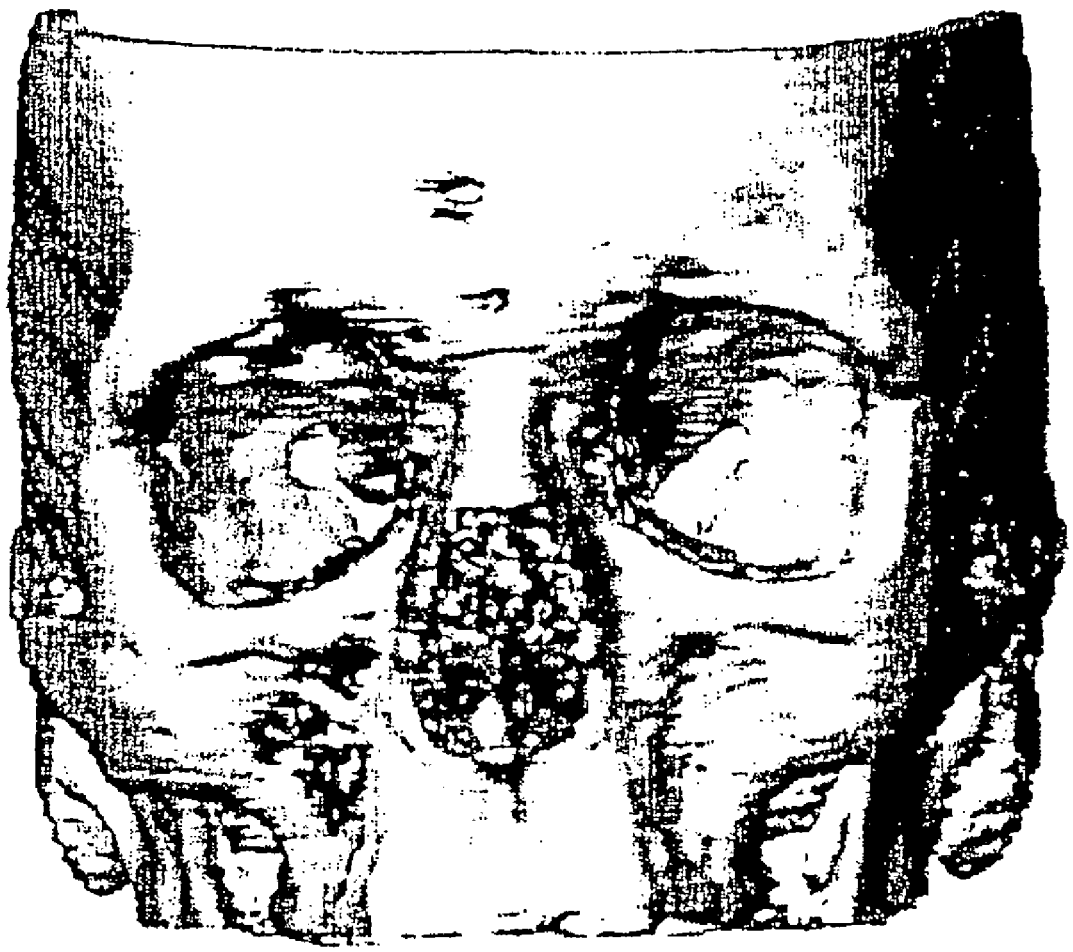
FIG. 1 illustrates an exemplary three-dimensional patient image.

FIG. 1 shows an example of a three-dimensional patient image that was generated from a two-dimensional diagnostic patient data set determined, for example, using computer tomography (CT) or magnetic resonance tomography (MRT). These data, for example, can be loaded into a computer with the aid of a software program, e.g., a program for planning surgical incisions (surgical planning software). The patient image shown in FIG. 1 does not show any landmarks. Conventionally, these would have to be identified by an operator (e.g., a physician) on the basis of the image, for example, by operating a mouse. As already stated above, identification of landmarks in accordance with the present invention is performed automatically.

Figure 2:
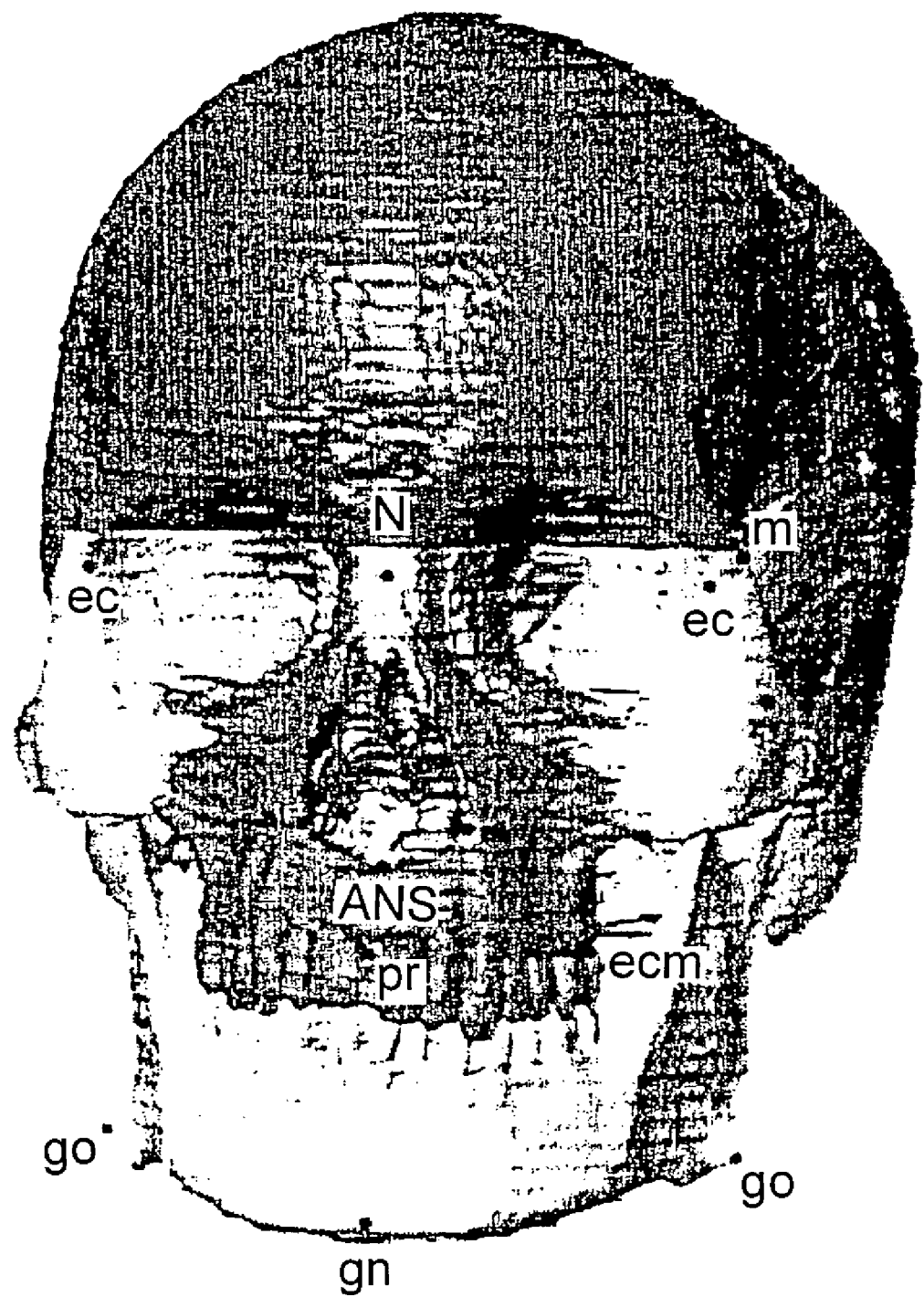
FIG. 2 illustrates an exemplary three-dimensional anatomical sample image together with landmarks.

To this end, reference is made to an anatomical sample image or sample data set, such as can be seen for example in FIG. 2. The anatomical sample image (here, a three-dimensional model from a digital anatomical atlas) is processed by a device in accordance with the invention. As can be seen in FIG. 2, in addition to the image of a human cranium, landmarks also can be seen that have been drawn in using black dots or points. Further, the landmarks include abbreviations such as N, pr, ANS, go, gn, etc. that describe a characteristic of the landmark (e.g., a name, etc.) As is evident, these anatomical landmarks are missing in the cranial image shown in FIG. 1. A device and method in accordance with the invention can preferably load the data shown in FIG. 2, for example into the program background, in order to form a starting point for determining the landmarks. The image data shown in FIG. 2 (sample image data) then can be converted into the patient data shown in FIG. 1 using a transformation means described herein. For example, a morphing algorithm or an algorithm for image fusion can be applied to the image data, wherein the anatomical landmarks shown in FIG. 2 undergo the same transformation as the image data (which represent the cranium) shown in FIG. 2. More specifically, the landmarks undergo the same transformation as that of image data situated at the same position of the landmarks.

Figure 3A:
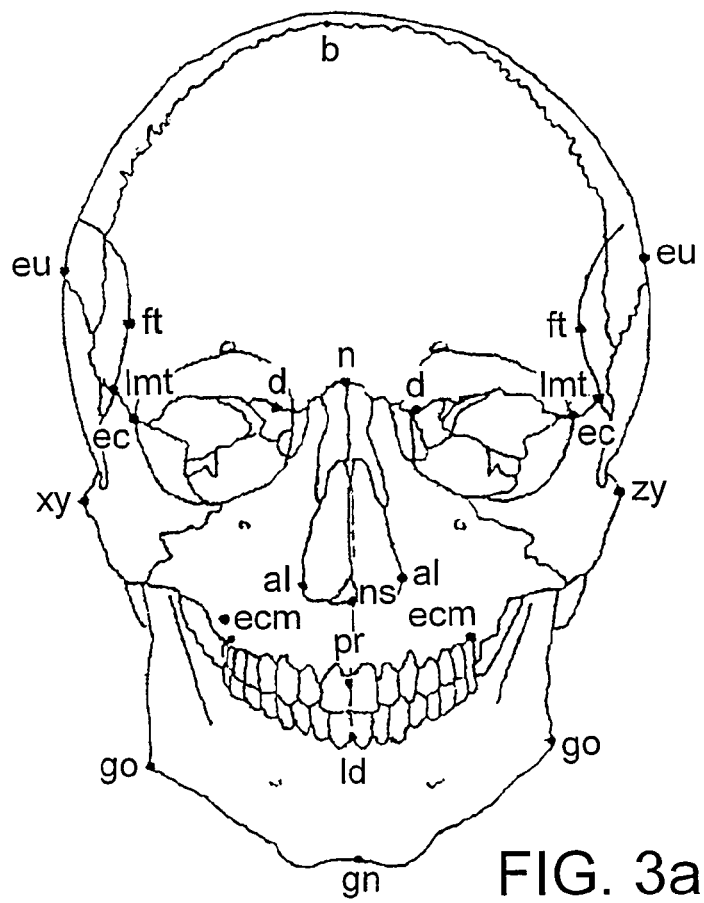
FIGS. 3a and 3b illustrate exemplary two-dimensional sample images.
Figure 3B:
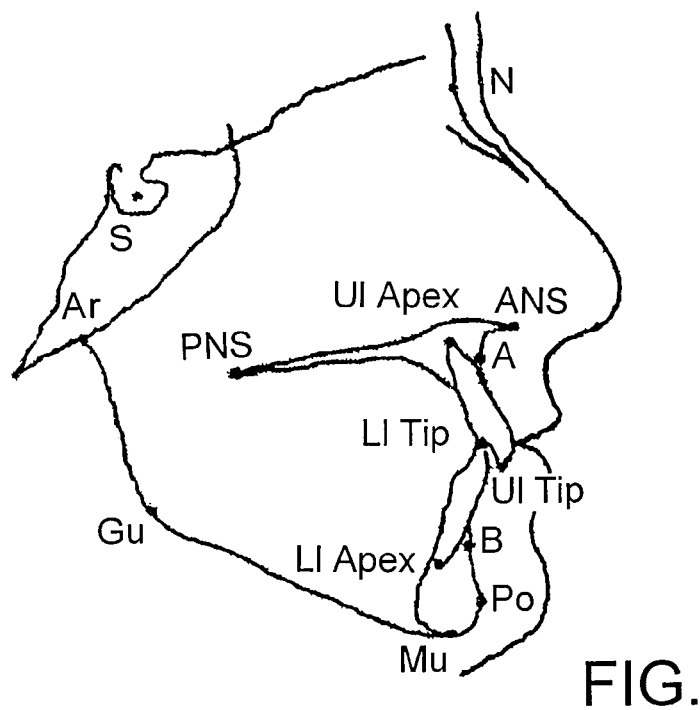

FIG. 3 shows exemplary two-dimensional sample images together with landmarks represented as black dots, wherein next to the dots, abbreviations are specified that designate the landmarks. The exemplary abbreviations are in accordance with the standard designations established in the medical field (e.g., al, ns, Id, pr, n, . . . ).

If the image-adapting transformation has converted the sample image into the patient image, then this results in the anatomical landmarks of the patient image also being converted. The image-adapting transformation can in particular be configured such that the converted data of the sample image match the patient image data to at least a predetermined accuracy. To this end, a similarity criterion can be defined for the algorithm and used as a terminating or target criterion.

Figure 4:
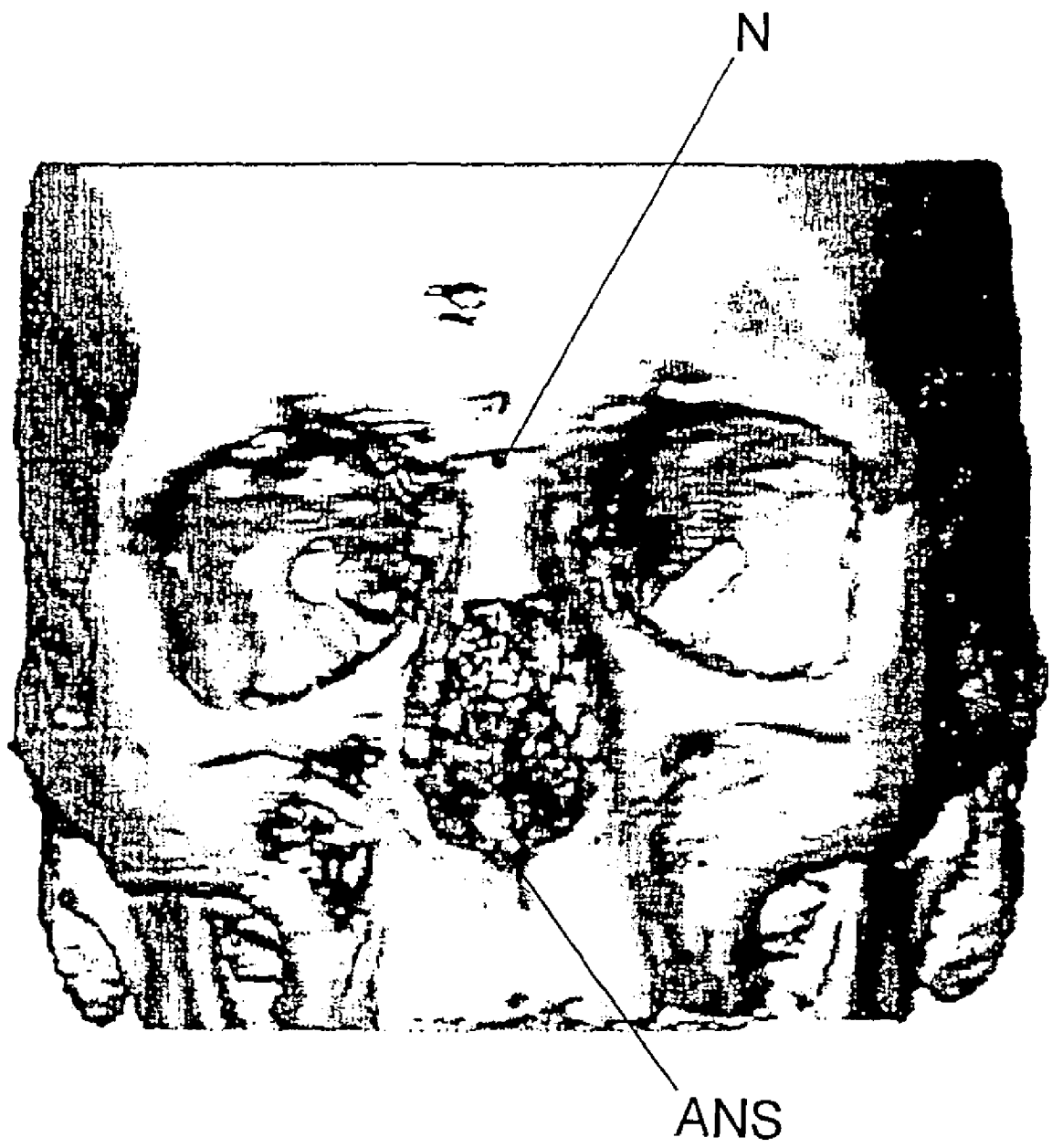
FIG. 4 illustrates a patient image together with determined landmarks.

FIG. 4 is an example of a patient image together with individual landmarks represented by dots. Two of the landmarks, namely the landmarks N and ANS, are identified in FIG. 4. They result automatically from the image-adapting transformation which converts the landmarks shown in FIG. 2 into the image shown in FIG. 1.

Figure 5:
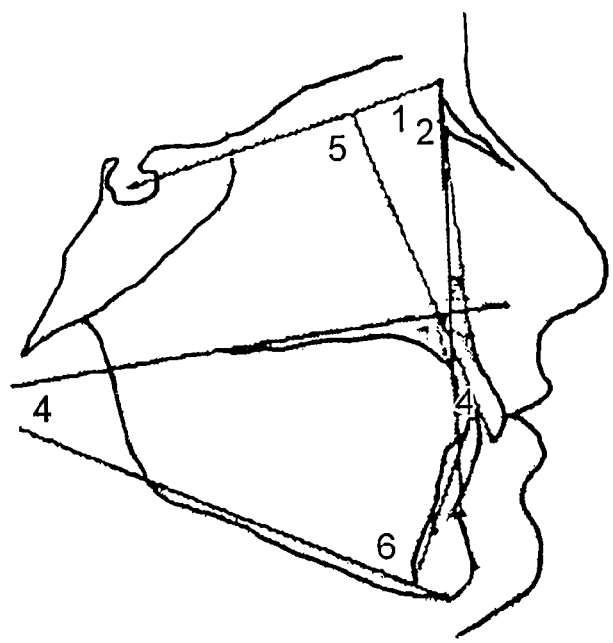
FIGS. 5 and 6 schematically illustrate how geometric values can be determined in accordance with the invention.
Figure 6:
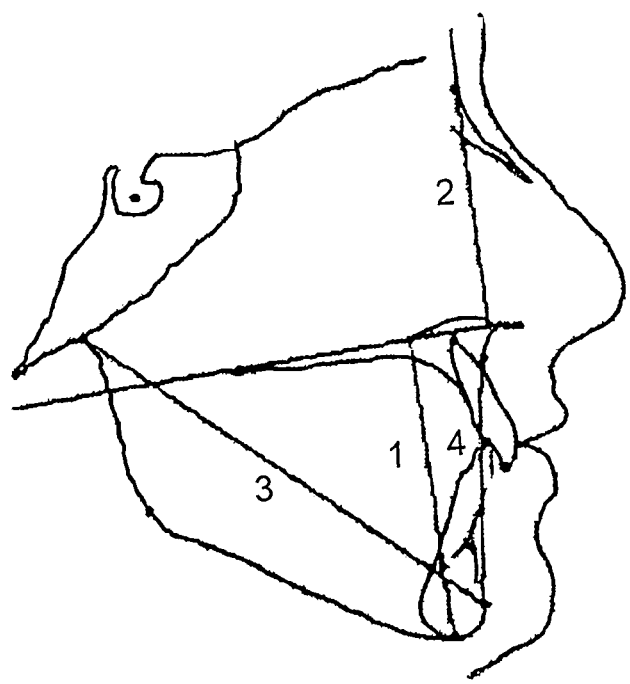

FIG. 5 and FIG. 6 show how anatomical values can be defined, wherein the lines designated by the numbers 1, 2, 3, 4, 5 and 6 connect different landmarks. The length of these lines, i.e., the distance between the landmarks, represents an example of geometric values. The same applies to the angles between the lines, which likewise represent an example of geometric values. The geometric values are preferably compared with nominal values, which, for example can be stored in a database and correspond to general standards in medical literature. A surgeon can thus identify the extent to which the patient corresponds to the standards and the extent to which there are deviations. The surgeon can in particular verify, for example in a jaw operation, the extent to which surgical incisions lead to deviations from the nominal values and/or the extent to which the geometric values of the patient can be converged with the nominal values by an operation (e.g., when correcting a set of upper teeth).

Figure 7:
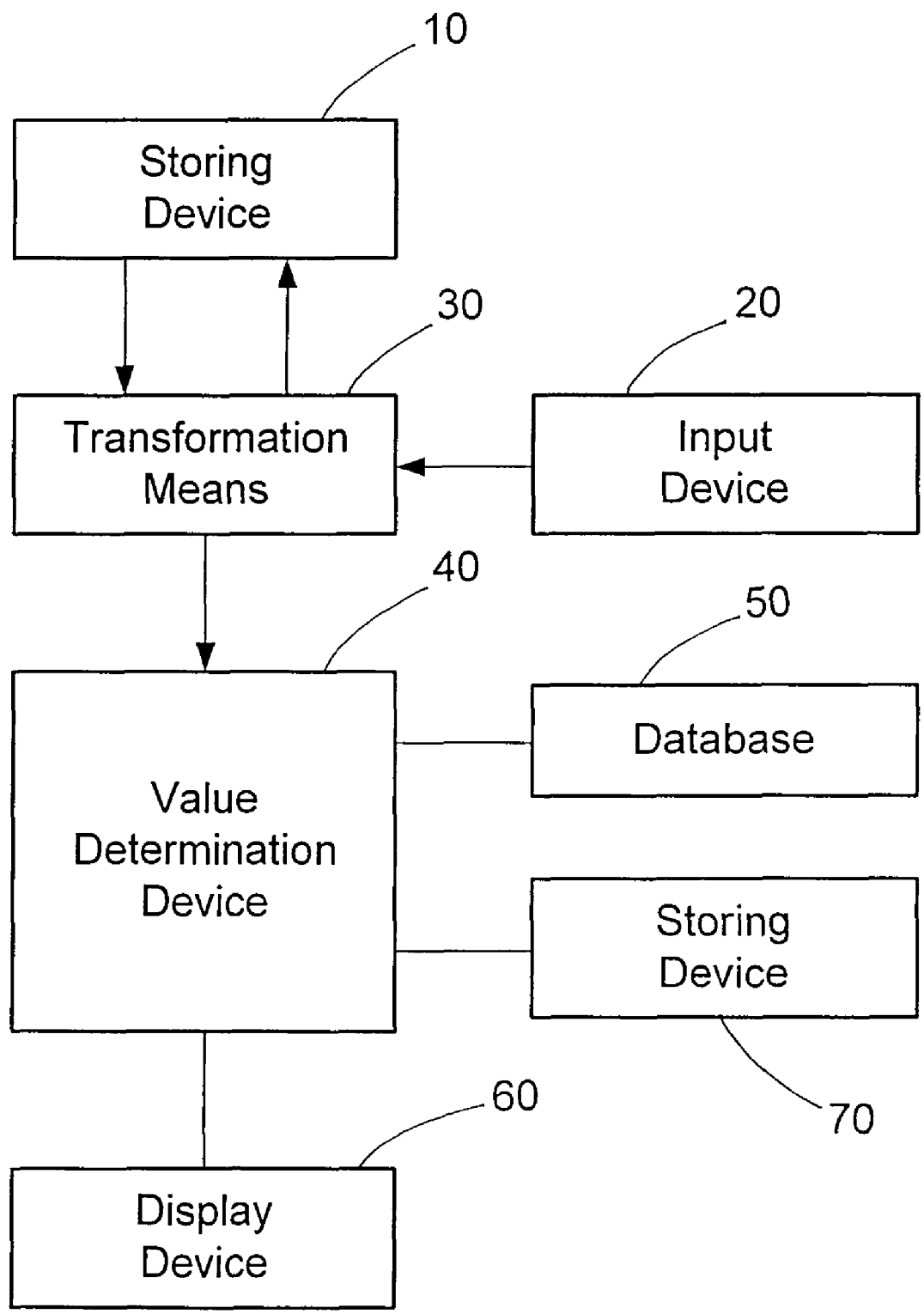
FIG. 7 illustrates a schematic layout of an automatic landmark determining device in accordance with the invention.
Figure 8:
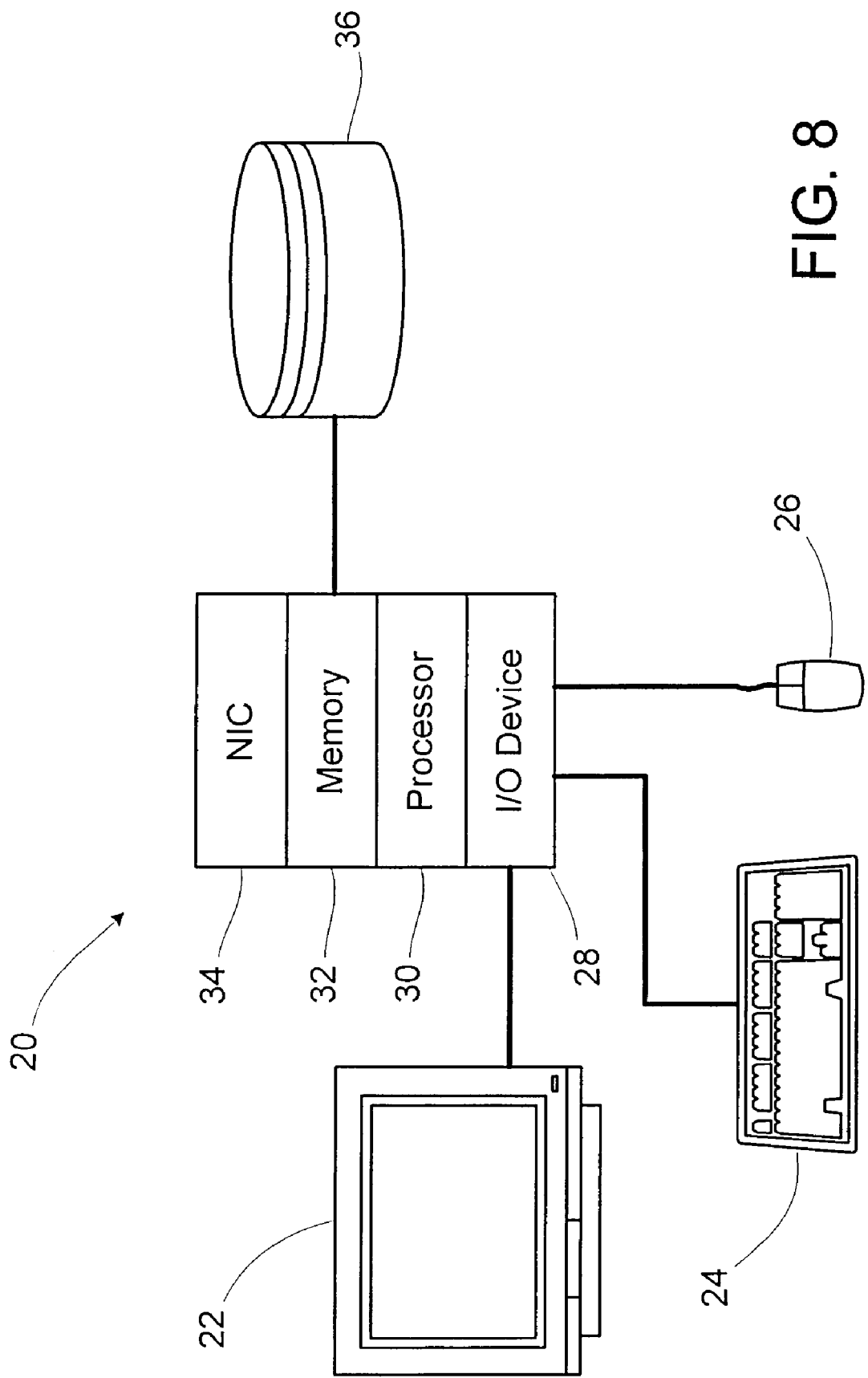
FIG. 8 is a block diagram of an exemplary computer system that can be used to implement the method described herein.

FIG. 7 schematically shows the layout of an exemplary automatic landmark determining device in accordance with the invention. A sample storing means 10, which, for example, can be designed as a hard disk in a computer, stores a digital anatomical atlas. The atlas comprises images to which anatomical landmarks are assigned. An input means 20 allows anatomical patient images to be inputted. The input means 20, for example, can be designed as a network interface and can be used to read or obtain data from a diagnostic imaging method. In another exemplary embodiment, the input means can be designed as a data drive.

The data from the sample storing means and from the input means are provided to the transformation means 30 (e.g., a processor, memory and logic stored in memory and executable by the processor) which performs the image-adapting transformation on the anatomical sample image, such that the anatomical sample image is converted into the patient image. The transformation means 30 preferably comprises a selecting means for selecting, on the basis of the patient image, an anatomical sample image from the anatomical database 10 which is most similar to the patient image. To this end, a database searching algorithm, for example, can be used that employs a pattern recognition algorithm. The sample storing means 10 thus preferably provides the transformation means 30 the anatomical sample image which it has selected on the basis of the patient image.

Once the landmarks have then been determined by the transformation means 30, they are preferably provided to the value determining means 40. The value determining means 40 determines the geometric values that depend on the relative location of the determined landmarks. The value determining means preferably comprises a comparing means that makes reference to a nominal value database 50 in order to compare the determined geometric values with nominal values. The comparison result is then provided from the value determining means 40, preferably to a display means 60 (for example a screen) which additionally or alternatively displays, in addition to said comparison result, the position of the landmarks, in particular in conjunction with the patient image data. The determined geometric values can alternatively or additionally be stored in a storing means 70. Additionally or alternatively, the patient image can also be stored, in particular together with the determined landmarks, in the storing means 70.

Moving now to FIG. 7 there is shown a block diagram of an exemplary computer 20 that may be used to implement the method described herein. The computer 20 may include a display 22 for viewing system information, and a keyboard 24 and pointing device 26 for data entry, screen navigation, etc. A computer mouse or other device that points to or otherwise identifies a location, action, etc., e.g., by a point and click method or some other method, are examples of a pointing device 26. Alternatively, a touch screen (not shown) may be used in place of the keyboard 24 and pointing device 26. The display 22, keyboard 24 and mouse 26 communicate with a processor via an input/output device 28, such as a video card and/or serial port (e.g., a USB port or the like).

A processor 30, such as an AMD Athlon 64® processor or an Intel Pentium IV® processor, combined with a memory 32 execute programs to perform various functions, such as data entry, numerical calculations, screen display, system setup, etc. The memory 32 may comprise several devices, including volatile and non-volatile memory components. Accordingly, the memory 32 may include, for example, random access memory (RAM), read-only memory (ROM), hard disks, floppy disks, optical disks (e.g., CDs and DVDs), tapes, flash devices and/or other memory components, plus associated drives, players and/or readers for the memory devices. The processor 30 and the memory 32 are coupled using a local interface (not shown). The local interface may be, for example, a data bus with accompanying control bus, a network, or other subsystem.

The memory may form part of a storage medium for storing information, such as application data, screen information, programs, etc., part of which may be in the form of a database 36 (such as the anatomical database 10 and/or the nominal value database 50). The storage medium may be a hard drive, for example, or any other storage means that can retain data, including other magnetic and/or optical storage devices. A network interface card (NIC) 34 allows the computer 20 to communicate with other devices.

A person having ordinary skill in the art of computer programming and applications of programming for computer systems would be able in view of the description provided herein to program a computer system 20 to operate and to carry out the functions described herein. Accordingly, details as to the specific programming code have been omitted for the sake of brevity. Also, while software in the memory 32 or in some other memory of the computer and/or server may be used to allow the system to carry out the functions and features described herein in accordance with the preferred embodiment of the invention, such functions and features also could be carried out via dedicated hardware, firmware, software, or combinations thereof, without departing from the scope of the invention.

Computer program elements of the invention may be embodied in hardware and/or in software (including firmware, resident software, micro-code, etc.). The invention may take the form of a computer program product, which can be embodied by a computer-usable or computer-readable storage medium having computer-usable or computer-readable program instructions, "code" or a "computer program" embodied in the medium for use by or in connection with the instruction execution system. In the context of this document, a computer-usable or computer-readable medium may be any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium such as the Internet. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner. The computer program product and any software and hardware described herein form the various means for carrying out the functions of the invention in the example embodiments.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. An automatic landmark determining device, comprising:
a storage device configured to store at least one anatomical sample image including anatomical image data of a body or body part, and at least one landmark corresponding to a characteristic location within the at least one anatomical sample image, said at least one landmark comprising information in addition to said anatomical image data;
an input device for inputting an anatomical patient image;
a transformation device configured to apply an image-adapting transformation to the at least one landmark, said image-adapting transformation corresponding to a transformation that converts the at least one anatomical sample image to the anatomical patient image.

2. The automatic landmark determining device according to claim 1, wherein the storage device stores an anatomical atlas that comprises a plurality of anatomical sample images and corresponding landmarks.

3. The automatic landmark determining device according to claim 1, wherein the transformation device is configured to use an image fusion algorithm or a morphing algorithm as the image-adapting transformation.

4. The automatic landmark determining device according to claim 1, wherein the storage device stores the at least one transformed landmark together with the anatomical patient image.

5. The automatic landmark determining device according to claim 1, further comprising a value determination device configured to determine geometric values that depend on a relative location of the at least one transformed landmark.

6. The automatic landmark determining device according to claim 5, wherein the value determination device includes a comparing device configured to compare the geometric values with nominal geometric values stored in a database of nominal geometric values.

7. The automatic landmark determining device according to claim 6, further comprising a display device that displays the comparison result.

8. The automatic landmark determining device according to claim 1, wherein the transformation device is configured to
a) transform the image data of the anatomical sample image together with the at least one landmark to obtain a new patient image that includes the at least one transformed landmark, or
b) transform the at least one landmark independent of the anatomical patient image or independent of the anatomical sample image such that the at least one transformed landmark is available for use with the anatomical patient image.

9. A method for analyzing patient images, comprising:
providing at least one anatomical sample image including anatomical image data of a body or body part together with corresponding landmarks, said landmarks comprising information in addition to said anatomical image data;
providing an anatomical patient image;
applying an image-adapting transformation to the landmarks, wherein the image-adapting transformation is configured to convert the anatomical sample image into the anatomical patient image; and
outputting the transformed landmarks.

10. The method according to claim 9, further comprising planning a surgical incision based on the transformed landmarks.

11. A computer program embodied on a non-transitory computer readable medium for analyzing patient images, wherein an anatomical patient image and at least one anatomical sample image including anatomical image data of a body or body part are provided, said at least one anatomical sample image including corresponding landmarks, said landmarks comprising information in addition to said anatomical image data, comprising:
code that applies an image-adapting transformation to the landmarks, wherein the image-adapting transformation is configured to convert the anatomical sample image into the anatomical patient image; and
code that outputs the transformed landmarks.

12. An automatic landmark determining device, comprising:
a processor and memory;
logic stored in the memory and executable by the processor, said logic including
logic that obtains at least one anatomical sample image including anatomical image data of a body or body part together with corresponding landmarks, said landmarks comprising information in addition to said anatomical image data;
logic that obtains an anatomical patient image; and
logic that applies an image-adapting transformation to the landmarks, wherein the image-adapting transformation is configured to convert the anatomical sample image into the anatomical patient image.

13. The automatic landmark determining device according to claim 12, further comprising:
a display device; and
logic that outputs the transformed landmarks on the display device.

* * * * *